United States Patent [19]

Igarashi et al.

[11] Patent Number: 4,673,636
[45] Date of Patent: Jun. 16, 1987

[54] MEDIUM FOR LYSINE DECARBOXYLATION TEST

[75] Inventors: Takeshi Igarashi, Tama; Toshihiko Endo, Fuji; Isei Koshi, Fujinomiya, all of Japan

[73] Assignee: Terumo Kabushiki Kaisha, Tokyo, Japan

[21] Appl. No.: 720,717

[22] Filed: Apr. 8, 1985

[30] Foreign Application Priority Data

May 9, 1984 [JP] Japan .................. 59-91065

[51] Int. Cl.$^4$ .................. C12Q 1/04; C12Q 1/10; C12Q 1/00; C12N 1/20
[52] U.S. Cl. .................. 435/34; 435/4; 435/38; 435/253
[58] Field of Search .................. 435/4, 34, 38, 253

[56] References Cited

U.S. PATENT DOCUMENTS 4,070,247 1/1978 Burt .................. 435/38
4,335,205 6/1982 Greenwood .................. 435/38

FOREIGN PATENT DOCUMENTS 0568691 1/1981 Japan .................. 435/180
0146596 9/1982 Japan .................. 435/34
0737452 6/1980 U.S.S.R. .................. 435/34

OTHER PUBLICATIONS

MacFaddin, J. F., Biochemical Tests for Identification of Medical Bacteria, 2nd edition, Williams & Wilkins, Baltimore, 1980, (pp. 59-63, 200-204).

Primary Examiner—Esther M. Kepplinger
Attorney, Agent, or Firm—Frishauf, Holtz, Goodman & Woodward

[57] ABSTRACT

A medium for lysine decarboxylation test comprises 2 to 7 g of yeast extract, 1 to 5 g of peptone, 0.5 to 1.5 g of glucose, 0.3 to 1 g of monalkali metal dihydrogen phosphate, 10 to 40 g of L-lysine mineral acid salt, 0.01 to 0.08 of 5'-pyridoxalphosphoric ester, and 0.04 to 0.1 g of a pH indicator, and has a pH value in the range of 5.5 to 6.5 when dissolved in 2 liter of water.

9 Claims, No Drawings

MEDIUM FOR LYSINE DECARBOXYLATION TEST

BACKGROUND OF THE INVENTION

1. Field of the Invention

This invention relates to a medium for testing a microorganism for biochemical behavior. More particularly, this invention relates to an improved medium to be used in performing lysine decarboxylation test on microorganisms such as enteric bacteria by the method of biochemical identification.

For administration of a proper medication to a patient of an infectious disease, it is essential to identify a pathogenic microorganism responsible for the disease, subjecting the patient to a sensitivity test, and selecting an effective medicine. In the identification of such a pathogenic microorganism, many biochemical tests are performed. One of them is an lysine decarboxylation test. The medium of this invention is advantageously used for the lysine decarboxylation test.

2. Description of the Prior Art

The lysine decarboxylation test is intended to detect a microorganism which decarboxylates L-lysine into cadaverine and carbon dioxide. At present, it is one of the most important tests performed on microorganisms for biochemical behavior. This test is carried out by culturing a given microorganism on a medium containing L-lysine and a pH indicator as main components. As the medium to be used in this test, a composition formed of trypton T, glucose, monosodium dihydrogen phosphate, L-lysine monohydrochloride, bromothymol blue, and purified water has been recently proposed [Japanese Patent Publication No. SHO 58(1983)-20,263]. This medium permits the time required for culture to be notably decreased as compared with the conventional countertype. Specifically, the culture time has been one to two days in the conventional medium, whereas it is four to five hours in the medium under discussion, making it possible to conduct the test and find the result of the test on one same day. Depending on the kind of the microorganism under test, however, the culture performed for four to five hours in this medium does not permit the reaction to proceed sufficiently for required evaluation. In this case, the culture time must be elongated and the evaluation of the test result made on the following day. In the circumstance, the desirability of developing a medium in which any microorganism can be cultured sufficiently in a matter of four to five hours to permit clear distinction between positive and negative test of the reaction has found growing approval.

For early medication, the identification of a pathogenic microorganism is desired to be carried out as rapidly as permissible. There are, however, times when the evaluation of the test result is compelled to be performed on the following day because of the convenience of the work involved in the test. In this case, the medium is desired to be such that the culture time is not rigidly specified and, therefore, the culture time may be elongated to suit the convenience of the work and, despite the elongation of the culture time, the reaction is not suffered to proceed excessively and the evaluation of the test result can be conducted accurately.

For the efficiency of work involved, many biochemical tests are frequently performed all at once by the use of a multi-well culture plate. Thus, it becomes necessary for culture times of different test items to be equalized to one another. Again in this case, the culture medium is desired not to involve any rigid limitation of culture time.

An object of this invention, therefore, is to provide a novel medium for lysine decarboxylation test.

Another object of this invention is to provide a medium which does not specifically limit culture time and enables the identification of the pathogenic microorganism to be performed on the same day as the culture is carried out or on the day following the culture.

A further object of this invention is to provide a medium for lysine decarboxylation test which permits a color reaction to produce a distinct color and enables the evaluation of test result to be effected with ease.

SUMMARY OF THE INVENTION

The objects described above are attained by a medium for the lysine decarboxylation test which is composed of 1 to 10 g of yeast extract, 1 to 10 g of peptone, 0.1 to 2 g of glucose, 0.2 to 2 g of a monoalkali metal dihydrogen phosphate, 5 to 50 g of L-lysine mineral acid salt, 0.005 to 0.1 g of 5'-pyridoxalphosphoric ester and 0.01 to 0.2 g of a pH indicator, which medium assumes a pH value in the range of 5.5 to 6.5 when dissolved in 1 liter of water.

DESCRIPTION OF THE PREFERRED EMBODIMENT

The medium of the present invention is an aqueous solution of yeast extract, casein-trypsin hydrolyzing peptone, glucose, monoalkali metal dihydrogen phosphate, L-lysine mineral acid salt, 5'-pyridoxalphosphoric ester and a pH indicator.

The composition of this medium comprises 1 to 10 g, preferably 2 to 7 g, of yeast extract, 1 to 10 g, preferably 1 to 5 g, of peptone, 0.1 to 2 g, preferably 0.5 to 1.5 g, of glucose, 0.2 to 2 g, preferably 0.3 to 1 g, of monoalkali metal dihydrogen phosphate, 5 to 50 g, preferably 10 to 40 g, of L-lysine mineral acid salt, 0.005 to 0.1 g, preferably 0.01 to 0.08 g, of 5'-pyridoxalphosphoric ester and 0.01 to 0.2 g, preferably 0.04 to 0.1 g, of a pH indicator.

5'-Pyridoxalphosphoric ester possesses an ability to promote the decarboxylation of lysine and serves to shorten the culture time. The yeast extract is intended to promote the enzymatic reaction.

The monoalkali metal dihydrogen phosphate is a pH adjuster. The alkali metal moiety of this phosphate is desired to be potassium or sodium. The L-lysine mineral acid salt is a substrate. The mineral acid salt is desired to be hydrochloride, sulfate, nitrate or phosphate. The pH indicator is not specifically limited. Examples of the pH indicator suitable for this invention include phenol red, bromothymol blue, bromocresol purple, cresol red, bromophenol red, chlorophenol red and the like. Among the pH indicators enumerated above, phenol red proves particularly desirable in the sense that the color produced in the color reaction is distinct enough to permit easy discrimination between positive and negative test even when the sample size is small.

The proportions of the components in the medium of the present invention are critical. In particular, the component of the monoalkali metal dihydrogen phosphate is fixed so that the pH value of the medium will fall in the range of 5.5 to 6.5, preferably 5.8 to 6.2, and the color of the color reaction will appear distinctly. Also the proportions of the lysine and the 5'-pyridoxalphosphoric ester are selected so as to permit reduction in the culture time.

The proportion of the pH indicator may be varied more or less, depending on the particular kind of pH indicator to be selected. In the case of phenol red, for example, the proportion is desired to fall in the range of 0.04 to 0.1 g/l.

The medium of this invention is prepared for use by dissolving the components in their respective proportions in water. In recent years, it is normal for numerous tests to be performed all at once by the use of a multi-well culture plate. For the medium of this invention to be used in this manner, it is poured into the wells of the culture plate and dried to be used as dry medium. In the test, a suspension of a microorganism is disposed in a prescribed volume to the individual wells and left standing therein to effect required culture for a prescribed length of time. By the change in color of the culture solution, the discrimination between positive test and negative test of the lysine decarboxylation reaction is effected.

The medium of the present invention is used in much the same way as the conventional medium for lysine decarboxylation test. With the medium of this invention, although the culture time can be reduced to the order of three to five hours, it is not specifically limited to that range. The culture may be performed for a longer period. Thus, the medium permits the evaluation of the test result either on the same day as the sample is taken or on the following day. The color produced in color test is so distinct as to permit easy discrimination between positive test and negative test of the reaction.

Now, one working example of the actual use of the medium of this invention in the lysine decarboxylation test will be described below.

EXAMPLES I-VI AND CONTROL I-III

| composition of medium | Example | | | | | | Control | | |
|---|---|---|---|---|---|---|---|---|---|
| | I | II | III | IV | V | VI | I | II | III |
| Trypton* | — | — | — | — | — | — | 2.5 | — | — |
| Yeast extract (g)** | 3.0 | 3.0 | 5.0 | 2.0 | 7.0 | 2.0 | — | 3.0 | 3.0 |
| Peptone (g)*** | 5.0 | 5.0 | 5.0 | 4.0 | 5.0 | 1.0 | — | 5.0 | 5.0 |
| Glucose (g) | 1.0 | 1.0 | 1.3 | 0.6 | 1.5 | 1.0 | 0.5 | 1.0 | 1.0 |
| Monosodium dihydrogen phosphate (g) | 0.6 | 0.6 | 0.7 | 0.4 | 1.0 | 0.3 | 0.5 | 0.6 | 0.1 |
| L-lysinemonohydrochloride (g) | 30.0 | 30.0 | 35.0 | 20.0 | 40.0 | 10.0 | 20.0 | 30.0 | 30.0 |
| 5'-Pyridoxal phosphoric ester (g) | 0.05 | 0.05 | 0.06 | 0.02 | 0.08 | 0.01 | — | 0 | 0.2 |
| Bromothymol blue (g) | — | — | — | — | 0.1 | — | 0.12 | — | — |
| Phenol red (g) | 0.06 | 0.04 | 0.05 | 0.05 | — | 0.05 | — | 0.06 | 0.06 |
| Purified water (liter) | 1 | 1 | 1 | 1 | 1 | 1 | 1 | 1 | 1 |
| pH | 6.0 | 6.0 | 6.0 | 6.0 | 6.2 | 5.8 | 6.0 | 6.0 | 6.0 |

*Casein-trypsin hydrolyzing peptone produced by Oxoid.
**Yeast extract produced by Difco.
***Casein-trypsin hydrolyzing peptone produced by Difco.

CULTURE CONDITIONS

The medium of this invention and control media having the compositions as shown above were dispensed in a unit volume of 50 $\mu$l to the wells of a culture plate and dried at 40° C. Separately various microorganisms were cultured on agar culture plates at 35° to 37° C. for 18 to 24 hours and suspended in 1.0 ml sterilized distilled water in a concentration of about 6 to $9 \times 10^8$ cells/ml. The suspensions were inoculated in a unit volume of 50 $\mu$l to the dry medium and, under a cover, cultured at 35° to 37° C. for a prescribed length of time. By the change in color of the resultant culture solutions, presence or absence of the lysine decarboxylation reaction was evaluated. The results are shown in Table 1.

TABLE 1

| Micro-organism | Medium of Example I | | Medium of Examples II-VI | | Control medium I | | Control medium II | | Control medium III | |
|---|---|---|---|---|---|---|---|---|---|---|
| | 4 to 5 hrs' culture | 16 to 20 hrs' culture | 4 to 5 hrs' culture | 16 to 20 hrs' culture | 4 to 5 hrs' culture | 16 to 20 hrs' culture | 4 to 5 hrs' culture | 16 to 20 hrs' culture | 4 to 5 hrs' culture | 16 to 20 hrs' culture |
| Escherichia coli | + | + | + | + | + | + | + | + | + | + |
| Enterobacter cloacae | — | — | — | — | — | — | — | — | — | — |
| Klebsiella pneumoniae | + | + | + | + | — | + | + | + | + | + |
| Klebsiella pneumoniae | + | + | + | + | ± — — | ± — + | + | + | + | + |
| Klebsiella pneumoniae | + | + | + | + | ± — — | + | ± — + | + | ± — + | + |
| Salmonella typhi | + | + | + | + | ± — — | ± — + | + | + | + | + |
| Salmonella spp. | + | + | + | + | — | ± — — | + | + | + | + |
| Serratia marcescens | + | + | + | + | ± — + | + | ± — + | + | ± — + | + |
| Serratia marcescens | + | + | + | + | ± — — | ± — + | ± — + | + | ± — + | + |

+: Color of positive test
—: Color of negative test
± — +: Intermediate color closer to color of positive test
± — —: Intermediate color closer to color of negative test It is noted from the results of Table 1 that the use of the medium of this invention in the lysine decarboxylation test permits accurate identification of microorganisms without reference to length of culture time. Thus, with the medium of this invention, the evaluation of test result can be carried out either on the same day as the sample is taken or on the following day, depending on the convenience of the work involved in the test.

In contrast, in the use of control media depending on the microorganism, the color produced after 4 to 5 hours' culture is not amply distinct to permit the evaluation of test test result on the same day as the sample is taken. Moreover, the fact that the medium of this invention is not rigidly restricted by the length of culture time proves highly convenient where numerous biochemical tests are carried out all at once.

What is claimed is:

1. A culture medium for a lysine decarboxylation test, comprising:
    2 to 7 g of yeast extract,
    1 to 5 g of peptone,
    0.5 to 1.5 g of glucose,
    0.3 to 1 g of monoalkali metal dihydrogen phosphate,
    10 to 40 g of L-lysine mineral acid salt,
    0.01 to 0.08 g of 5'-pyridoxalphosphoric ester, and
    0.04 to 0.1 g of a pH indicator,
said culture medium exhibits a pH value of from 5.5 to 6.5 when dissolved in 1 liter of water.

2. The medium according to claim 1, wherein the pH value of the medium is from 5.8 to 6.2.

3. The medium according to claim 1, wherein said monoalkali metal dihydrogen phosphate is potassium salt or sodium salt.

4. The medium according to claim 1, wherein said L-lysine mineral acid salt is at least one salt selected from the group consisting of hydrochloride, sulfate and phosphate.

5. The medium according to claim 1, wherein said pH indicator is one compound selected from the group consisting of phenol red, bromothymol blue, bromocresol purple, cresol red, chlorophenol red and bromophenol red.

6. The medium according to claim 5, wherein said pH indicator is phenol red.

7. The medium according to claim 2, wherein said monoalkali metal dihydrogen phosphate is potassium salt or sodium salt and said pH indicator is phenol red.

8. The medium according to claim 7, wherein said L-lysine mineral acid salt is at least one salt selected from the group consisting of hydrochloride, sulfate and phosphate.

9. The medium according to claim 8, wherein said pH indicator is phenol red.

* * * * *